United States Patent [19]

Popovich et al.

[11] E Patent Number: Re. 31,688

[45] Reissued Date of Patent: Sep. 25, 1984

[54] METHOD AND APPARATUS FOR CONTINUOUS PLASMAPHERESIS

[75] Inventors: Robert P. Popovich; Jack W. Moncrief, both of Austin, Tex.; Glen D. Antwiler, Westminister, Colo.

[73] Assignee: Hemotherapy, Inc., Austin, Tex.

[21] Appl. No.: 354,054

[22] Filed: Mar. 2, 1982

Related U.S. Patent Documents

Reissue of:

[64] Patent No.: 4,191,182
Issued: Mar. 4, 1980
Appl. No.: 836,214
Filed: Sep. 23, 1977

[51] Int. Cl.[3] ..... A61M 1/03

[52] U.S. Cl. ..... 604/6; 210/195.2; 210/321.3; 210/433.2; 210/651; 210/927

[58] Field of Search ..... 210/195.2, 321.3, 433.2, 210/434, 651, 927; 128/214; 422/44; 604/6

[56] References Cited

U.S. PATENT DOCUMENTS

| | | |
|---|---|---|
| 2,864,506 | 12/1958 | Hiskey . |
| 3,211,645 | 10/1965 | Ferrari . |
| 3,441,136 | 4/1969 | Serfass et al. . |
| 3,483,867 | 12/1969 | Markovitz . |
| 3,488,766 | 1/1970 | Rigopulos . |
| 3,489,145 | 1/1970 | Judson et al. . |
| 3,539,300 | 11/1970 | Stone . |
| 3,556,302 | 1/1971 | Agranat . |
| 3,560,377 | 2/1971 | Loeffler . |
| 3,567,031 | 3/1971 | Loeffler . |
| 3,579,441 | 5/1971 | Brown . |
| 3,619,423 | 11/1971 | Galletti . |
| 3,705,100 | 12/1972 | Blatt et al. . |
| 3,731,680 | 5/1973 | Wright et al. . |
| 3,765,536 | 10/1973 | Rosenberg . |
| 3,788,319 | 1/1974 | Gillette . |
| 3,795,318 | 3/1974 | Crane et al. . |
| 3,880,759 | 4/1975 | Van Assendelft . |
| 3,900,398 | 8/1975 | Gillette . |
| 4,013,072 | 3/1977 | Jess . |
| 4,013,564 | 3/1977 | Nose . |
| 4,105,547 | 8/1975 | Sandblom . |

OTHER PUBLICATIONS

"The Effects of Membrane Diffusion and Ultrafiltration Properties on Hemodialyzer Design and Performance", Popovich et al, Chemical Engineering Progress, vol. 67, No. 114, pp. 105–115 (1971).

"Transfer of Chemical Species Through a Protein Gel", Dorson et al., vol. XVII, Trans. Amer. Soc. Artif. Int. Organs, pp. 287–292 (1971).

"Plasma Exchange in Patients with Fulminant Hepatic Failure", Buckner et al., Arch. Intern. Med./vol. 132, pp. 487–492 (Oc. 1973).

"Characterization of Possible 'Toxic' Metabolites in Uremia and Hepatic Coma Based on the Clearance Spectrum for Larger Molecules by the ACA Microcapsule Artificial Kidney", Change et al., vol. XIX, Trans. Amer. Soc. Artif. Int. Organs, pp. 314–319 (1973).

"Initial Trials of Molecular Separation Artificial Kidney", Dorsen et al., vol. XIX, Trans. Amer. Soc. Artif. Int. Organs, pp. 119–125 (1973).

"Clinical Experience with Intermittent Hemodiafiltration", Henderson et al., vol. XIX, Trans. Amer. Soc. Artif. Int. Organs, pp. 119–125 (1973).

"Plasma Fractionation in the United States", Ness et al, JAMA, vol. 230, No. 2, pp. 247–250 (Oct. 14, 1974).

(List continued on next page.)

*Primary Examiner*—Ferris H. Lander
*Attorney, Agent, or Firm*—Arnold, White & Durkee

[57] ABSTRACT

A process and apparatus are provided for continuously separating blood into plasma and cellular component fractions and returning the latter to the subject in admixture with a makeup fluid. The separation is effected by continuously ultrafiltering the subject's blood at specified shear stresses and pressures employing a membrane ultrafilter, preferably having a pore size of 0.45 microns, and a disclosed flow system.

28 Claims, 2 Drawing Figures

OTHER PUBLICATIONS

"Microemboli-Free Blood Detoxification Utilizing Plasma Filtration", Castino et al., Amer. Soc. Artif. Int. Organs, pp. 637-644 (1976).

"Investigation of Factors Controlling the Rate of Plasma Filtration with Microporous Membranes", Lysaght et al., AICHE 83rd National Meeting, Houston, Texas, Mar. 20-24, 1977.

Buckner et al., "Plasma Exchange with NCI-IBM Blood Cell Separator", Rev. Fr Etud Clin Biol vol. 14: 803-805, Oct. 1969.

Graw, Jr. et al., "Plasma Exchange Transfusion for Hepatic Coma New Technique", Human Tumor Cell Bio. Br., Natl. Cancer Inst.; Jan.-Feb. 1970, Transfusion pp. 26-32.

"Membrane Separation", Osborn et al., T884,001, Def. Pub., published 3/09/71, 884 O.G. 433.

METHOD AND APPARATUS FOR CONTINUOUS PLASMAPHERESIS

Matter enclosed in heavy brackets [ ] appears in the original patent but forms no part of this reissue specification; matter printed in italics indicates the additions made by reissue.

BACKGROUND OF THE INVENTION

In one aspect the present invention relates to plasmapheresis, that is, the separation of blood into a plasma fraction and a cellular component fraction. In another aspect, the present invention relates to plasmapheresis effected by ultrafiltration on a continuous basis, that is, a process whereby blood is withdrawn from a donor, separated into cellular component and plasma fractions, and the cellular components returned, in admixture with an appropriate amount of replacement fluid, to the donor at approximately the rate at which blood is being withdrawn. In still a further aspect, the present invention relates to an apparatus for the continuous separation of blood into plasma and cellular component fractions by ultrafiltration.

To appreciate the nature of the present invention, as well as the difficulties and complications which attend the separation of blood into cellular component and plasma fractions, a brief discussion of the makeup of blood is useful. Approximately 45% of the volume of blood is in the form of cellular components. These cellular components include red cells, also referred to as erythrocytes, white cells, also referred to as leukocytes, and platelets. Plasma makes up the remaining 55% of the volume of blood. Basically, plasma is the fluid portion of the blood which suspends the cells and comprises a solution of approximately 90% water, 7% protein and 3% of various other organic and inorganic solutes. As used herein, the term "plasmapheresis" refers to the separation of a portion of the plasma fraction of the blood from the cellular components thereof. Thus, plasmapheresis effected by ultrafiltration is to be distinguished from ultrafiltration of blood into a fraction containing cellular materials and the protein constituents of the plasma and a fraction comprising the aqueous portion of the plasma.

Separation of blood into a plasma fraction and a cellular component fraction is desirable for many medical reasons. For example, separation of blood into plasma fractions and cellular component fractions provides for a collection of plasma alone, with the cellular components being returned to the donor with a suitable portion of replacement fluid. Thus, continuous plasmapheresis provides for the collection of plasma from donors without the removal of the cellular components of the blood. Secondly, continuous plasmapheresis can be used therapeutically to remove pathogenic substances contained in the plasma portion of the blood. This can be accomplished by separating the cellular components from the diseased plasma and returning the cellular components to the patient in admixture with a suitable replacement fluid, or by further fractionating the patient's plasma to remove the unwanted substances and returning a major portion of the patient's plasma with the cellular components. Finally, a continuous plasmapheresis process can be employed for diagnostic purposes wherein plasma is separated on a continuous basis from the cellular components and analyzed to detect disease-causing substances or conditions therein.

In the past, ultrafiltration has been used on a continuous basis as a substitute for, or in combination with, dialysis methods in artificial kidneys and the like and has also been employed in batch-type plasmapheresis processes. For example, U.S. Pat. No. 3,579,441 to Brown, issued May 18, 1971, discloses a means for purifying the blood by continuously ultrafiltering the blood to separate macromolecular substances having molecular weights higher than 10,000, or so, and generally at least 40,000–50,000 which includes blood cells, fat droplets, lipids, high molecular weight polypeptides and the like from the remaining ultrafiltered aqueous portion of the blood. Such operations are not true plasmapheresis processes, as defined herein, because blood is separated not into plasma and cellular component fractions but rather into macromolecular fractions (containing cellular components and portions of the plasma) and a low molecular weight fraction which contains the waste products which must be removed in an artificial kidney-type process. Further, ultrafiltration has been used for plasmapheresis on a noncontinuous basis. For example, U.S. Pat. No. 3,705,100 to Blatt et al., issued Dec. 5, 1972, discloses a process and apparatus for a blood fractionating process. However, the process and apparatus disclosed therein is for the fractionating of blood on a batch basis, that is, on a noncontinuous basis whereby blood is held in a reservoir and then circulated in a spiral flow over an ultrafiltration membrane to effect separation.

In any plasmapheresis-type process effected by ultrafiltration there are various problems which occur during the fractionating of the blood by passing it in a parallel flow pattern over a membrane, with a transmembrane pressure sufficient to push the plasma portion of the blood therethrough, while allowing the cellular component portion of the blood to remain thereon. One of these problems is that the flow rates must be controlled fairly closely. Thus, if the flow rate employed is too fast, turbulence will occur within the ultrafiltration cell which may cause hemolysis and the general destruction of cellular components. On the other hand, if flow rates and transmembrane pressures are not controlled adequately the cellular and macromolecular components of the blood will tend to clog up the membrane thus significantly slowing the ultrafiltration rate. Such clogging can also cause hemolysis to occur. While the above stated problems attend any ultrafiltration procedure employed to fractionate blood there are several other important problems which attend the continuous plasmapheresis of blood wherein cellular components of the blood are continually returned to the patient with an amount of replacement fluid equal to the volume of plasma extracted from the blood. Thus, one of the basic problems of plasmapheresis is that some of the cellular components of the blood, such as platelets for example, are very fragile and easily destroyed and therefore must be returned to the patient undergoing plasmapheresis within a time period shorter than the useful life thereof. Blood which is stored in blood banks and the like typically does not contain sufficient amounts of viable platelets, because the blood has been outside the body longer than the useful life thereof. Another problem attending continuous plasmapheresis includes the tendency of blood which is being separated by ultrafiltration to have damage occur to the clotting factors thereof. Basically there are approximately a dozen different clotting factors which can be affected, and, of course, re-injecting the cellular components back into a patient's system where the clotting factors have been adversely effected could result in a condition similar to hemophilia. Thirdly, denaturing of proteinaceous materials contained in the blood can be a problem if the blood is subjected to varying conditions outside the body for extended periods of time.

Thus, while ultrafiltration has been employed in the past either in a plasmapheresis batch system, or in a blood fractionating process in artificial kidney devices, there is not at present a process and apparatus which provides for the continuous separation of blood into plasma fractions and cellular component fractions, wherein the cellular component fractions are continuously returned to the donor with an effective amount of replacement fluid to thereby continuously separate the donor's plasma for use in transfusions, or diagnostic, or therapeutic procedures.

SUMMARY OF THE INVENTION

The process and apparatus of the subject invention provide for the fractionation of blood into a cellular component fraction and a plasma fraction on a continuous basis. Thus, according to the process described herein, a blood feed conduit communicating with a blood vessel, through a cannula formed therein, delivers whole blood to the apparatus further described hereinbelow which includes means for ultrafiltering and thereby separating the cellular components of the blood from the plasma fraction thereof. The cellular components are then returned in admixture with an appropriate amount of replacement fluid, through a second conduit and cannula formed in a second blood vessel of the patient or donor. Therefore, the apparatus and process described herein provide for the continuous separation of plasma from the cellular components of the blood with return of the latter with an appropriate amount of replacement fluid to the subject. The process is hereinafter referred to as continuous plasmapheresis.

Continuous plasmapheresis is accomplished by continually withdrawing whole blood from a blood vessel and pumping same through an ultrafiltration chamber to effect separation of plasma and cellular components. The blood passes in laminar flow, parallel to the plane of the ultrafiltration membrane at flow rates sufficient to create shear stress across the ultrafilter membrane of from about 10 dynes/cm$^2$ to about 1000 dynes/cm$^2$, a preferred range being from about 150 dynes/cm$^2$ to about 600 dynes/cm$^2$. The membrane has a pore size sufficient to allow the plasma components to pass therethrough but retain cellular components thereon. Generally pore sizes of from about 1.0 to about 0.05 microns can be employed, a preferred range being from about 1.0 to about 0.1 microns, membranes having a pore size of approximately 0.45 microns being especially preferred. Transmembrane pressures of from about 50 mmHg to about 700 mmHg are employed to separate the blood into cellular component and plasma fractions, a preferred range being about 100 to about 400 mmHg. Transmembrane pressures of about 200 mmHg are especially preferred. The cellular components are then admixed with a suitable amount of replacement fluid which can be clean plasma, an aqueous solution of dextran, normal serum albumin, normal saline, or any other suitable plasma substitute, and the replacement fluidcellular component mixture is then returned to the subject, on a continuous basis, through a cannula in a second blood vessel. A single vessel can be employed with the use of a double lumen catheter.

In order to accomplish the above process a special apparatus basically comprising one or more ultrafiltration cells in combination with pumping means, conduits, and pressure regulating and sensing devices is provided. The apparatus includes an ultrafiltration cell comprising at least one filter membrane separating the cell into filtering and filtrate chambers. The filtering chamber has an inlet and outlet thereto. A blood input pumping means is connected to the inlet of the filtering chamber portion of the ultrafiltration cell for delivering blood at a preselected flow rate. Recycling pumping means can also be connected via conduits between the inlet and outlet of the filtering chamber of the ultrafiltration cell. This recycling pumping provides for continuous movement of the blood, through the filtering chamber of the ultrafiltration cell at a rate sufficient to obtain the necessary shear rate when the flow of whole blood alone is insufficient. A plasma pumping means is connected to the outlet of the filtrate chamber for removing the plasma fraction therefrom. Transmembrane pressure is regulated either by adjusting the plasma pumping means, or the blood input and recycling pumping means, or both, or by restricting flow out of the ultrafiltration cell.

Additionally, replacement fluid pumping means, interconnected with the plasma pumping means in a manner such that the plasma and replacement fluid pumping means operate at substantially the same rate, is provided, thus insuring that the amount of replacement fluid added to the system is substantially equal to the amount of plasma being withdrawn.

In a preferred embodiment of the subject invention, the rate of ultrafiltration (or flux) through the ultrafilter membrane is increased by providing a plasma recycling flow through the filtrate chamber of the ultrafiltration cell, said flow being parallel to that of the whole blood in the filtering chamber, to thereby provide a constant transmembrane pressure across the entire flow path length of the membrane.

SHORT DESCRIPTION OF THE DRAWINGS

FIG. 1 is a schematic representation of one embodiment of the plasmapheresis apparatus of the present invention; and FIG. 2 is a schematic representation of a second embodiment of the plasmapheresis apparatus of the present invention.

DETAILED DESCRIPTION

Figure 1:
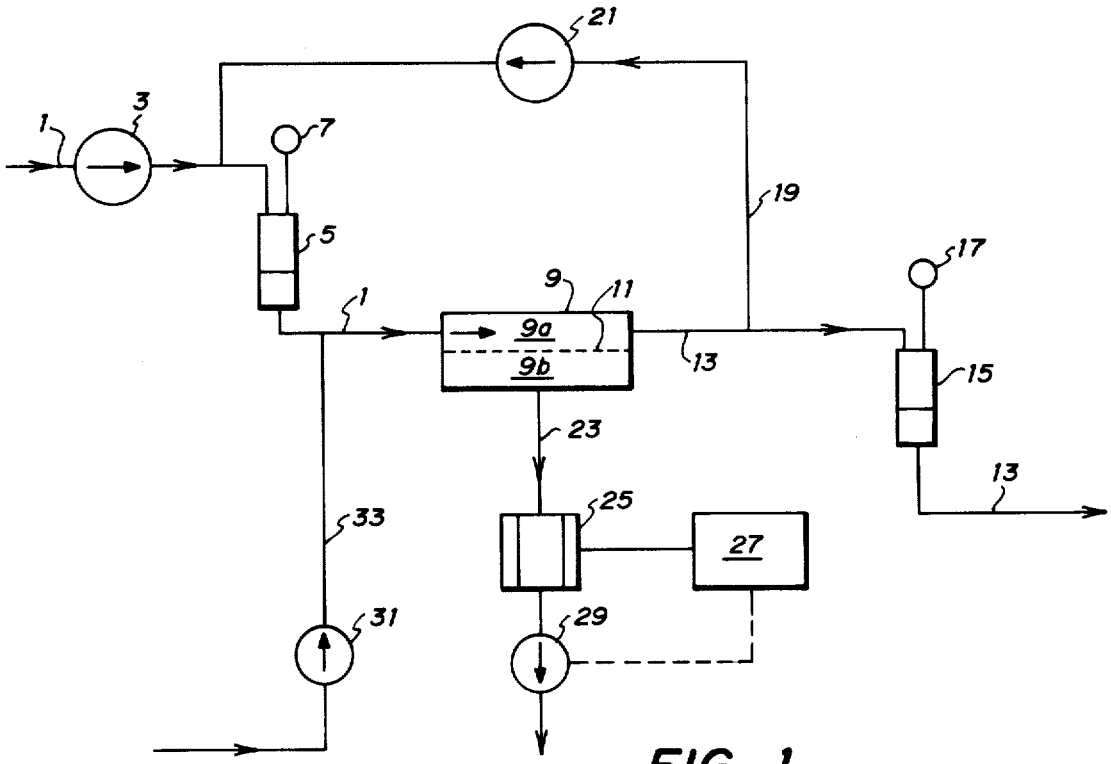

It has been discovered that in order to continuously separate blood into a plasma fraction and a cellular component fraction and return the cellular components with an appropriate amount of replacement fluid to the patient or donor specific process conditions must be maintained during the ultrafiltration of the blood. Specifically, it has been discovered that by creating specific shear stresses of the blood as it flows over the membrane of the ultrafilter at transmembrane pressures of from about 100 to about 400 mm of mercury and employing an ultrafiltration membrane having a pore size of 0.45 microns fabricated from cellulose nitrate or regenerated cellulose the prior art problems of hemolysis, clogging, and polarization of membrane materials can be overcome and continuous plasmapheresis obtained.

Proper shear stress over the membrane is provided by recycling a portion of the cellular components at the outlet of the ultrafiltration cell to the inlet of the ultrafiltration cell. In this manner, the recycled portion admixes with the fresh incoming whole blood and provides for flow rates through the ultrafiltration cell in excess of those obtained from the input of the blood pumping means alone which is delivering blood to the ultrafiltration cell from a donor. In a preferred embodiment, further described below, replacement fluids are also added at the inlet of the ultrafiltration cell further increasing the volumetric flow rate (and therefore shear stress) through the ultrafiltration cell. Means for regulating the flow of the blood through the filtering chamber of the ultrafiltration cell can be provided at both the inlet and the outlet thereof so that a preferred pressure and flow rate across the filtering side of the membrane can be maintained.

A plasma pumping means is provided for removing plasma from the filtrate side of the ultrafiltration cell at a rate sufficient to insure that preferred transmembrane pressures of from about 100 to about 400 and preferably about 200 mm of mercury are maintained. A pressure transducer for sensing and measuring the pressure on the filtrate side of the ultrafiltration cell is provided for regulation purposes. The plasma pumping means is interconnected, for example by means of a common drive shaft, with a replacement fluid pump such that replacement fluids are added to the system at substantially the same rate at which plasma is being withdrawn. Thus, the volumetric flow rates in and out of the continous plasmapheresis apparatus of the subject invention will be essentially equal during operation. Replacement fluids are admixed with the cellular components either by connecting the replacement fluid conduit with the outlet from the ultrafiltration cell or the input thereof as disclosed above. In the latter case the replacement fluids dilute the cellular components which are reconstituted to their normal levels in the ultrafiltration cell. This prevents the cellular components from being densely packed which can result in excessive hemolysis. The replacement fluids employed can either be plasma, or a suitable substitute therefor.

In another embodiment of the present invention a unique plasma filtrate flow, parallel to that of the flow of blood over the filtering side of the ultrafiltration membrane, is employed in order to obtain relatively constant transmembrane pressures over the entire membrane surface. This is accomplished by recycling plasma filtrate through the filtrate chamber of the ultrafiltration cell in the same direction and parallel to the flow of the blood which is being ultrafiltered in the filtering chamber of the ultrafiltration cell. By regulating the inlet and outlet pressures of the plasma recycle such that the pressure drop across the filtrate chamber of the ultrafiltration cell equals the pressure drop of the blood across the filtering chamber substantially constant transmembrane pressures are obtained. This is important because there is a maximum allowable transmembrane pressure which can be employed at a given shear rate without causing excessive damage to the cellular components. The result is that ultrafiltration rates, or fluxes, are increased in the order of twice that when plasma filtrate is removed from the filtrate chamber without such recycling. In the embodiment described previously wherein plasma is simply removed from the filtrate chamber of the ultrafiltration cell the filtrate side of the membrane is essentially at a uniform pressure. Thus, transmembrane pressure is high (or at the maximum) at the portion of the membrane adjacent the blood inlet side of the filtering chamber and progressively becomes smaller as the blood flows through the channel toward the blood outlet of the filtering chamber. However, by providing a pressure drop of plasma filtrate across the filtrate side of the membrane which is equal to the pressure drop of the blood flowing across the filtering side of the membrane the transmembrane pressure is kept constant across the entire flow path of the blood through the ultrafiltration cell. This allows for the use of long filtering chamber flow paths which would otherwise be prohibited because of excessive inlet transmembrane pressures with concomitant cellular destruction. This is an important design criteria for the manufacture of coil type ultrafiltration cells.

Now referring to FIG. 1, a detailed description of the continuous plasmapheresis process of the subject invention according to a preferred embodiment will be described. Blood enters the processing system of the subject invention via conduit 1 which communicates with a blood vessel of the subject via a suitable catheter. The conduit can comprise various types of flexible plastic tubing including, for example, non-thrombogenic materials such as heparinized polytetrafluoroethylene, heparinized surgical grade silicon rubber, and the like. Generally, conduits useful in the present invention can be flexible tubing having inner diameters of from about 1/16 inch to about ⅜ inch so as to be sufficient to provide the necessary flow rates required by the process of the subject invention. The blood flow in conduit 1 will normally be from about 20 ml/minute to about 400 ml/minute depending on the blood vessel and the physical characteristics of the subject, if the process is being run on a human. Therefore, the flow rate in conduit 1 is regulated via inlet pumping means 3 which can, for example, be a common type of pump used in medical apparatus such as a peristaltic pump. Inlet conduit 1 can then empty into a drip cell 5 in order to insure that any entrapped gas bubbles will be removed prior to the introduction of the blood into the ultrafiltration cell 9 further described hereinbelow. A pressure gauge, or other pressure indicating instrument, 7 can be employed for monitoring the inlet pressure of the blood flow coming from inlet pumping means 3. Inlet conduit 1 empties into ultrafiltration cell 9 which basically comprises a filtering chamber 9a at the top portion thereof and a filtrate chamber 9b at the lower portion thereof, the two chambers being separated by an ultrafiltration membrane 11. The ultrafiltration cell, more fully described hereinbelow, partially separates the whole blood into a cellular fraction which remains on top of the ultrafiltration membrane 11 within filtering chamber 9a and a plasma fraction which passes through ultrafiltration membrane 11 and into filtrate chamber 9b. The concentrated cellular components are passed from the ultrafiltration cell via outlet conduit 13 and a portion thereof, in admixture with makeup fluid, which has been added to the system in a manner described below, are returned to the subject via drip cell 15 which prevents the transmission of air bubbles to the patient and a suitable catheter inserted in a blood vessel of the subject. A second pressure indicating instrument 17 can be used to monitor the pressure at the outlet end of the ultrafiltration cell.

A portion of the cellular component fraction admixed with replacement fluid is recycled through the ultrafiltration cell via recycle conduit 19 and recycle pumping means 21. The amount of fluid recycled in this manner will depend upon the flow rates desired to maintain the approximate shear rates in the particular ultrafiltration cell employed which will generally be in a range of from about 10 dynes/cm$^2$ to about 1000 dynes/cm$^2$ with a preferred range of from about 150 to about 600 dynes/cm$^2$.

The plasma fraction flowing into filtrate chamber 9b through ultrafiltering membrane 11 is removed via plasma outlet conduit 23. Plasma outlet conduit 23 communicates with pressure sensing means 25 which in turn controls the pumping rate of plasma pumping means 29. In a preferred embodiment, pressure sensing means 25 can comprise a pressure transducer which generates an electrical signal of varying strength in response to the pressure in plasma outlet conduit 23. The electrical signal generated by such a transducer is then communicated to pump control means 27 which can comprise, for example, a rheostat which in turn is connected electrically to an electrically driven pump (plasma pumping means 29). In this manner, the rate at which plasma pump 29 operates can be controlled such that the pressure in plasma outlet conduit 23 never varies from that necessary to maintain optimum transmembrane pressures, regardless of the rate of ultrafiltration. Preferably the pressure in filtrate chamber 9b is kept at about atmospheric pressure at all times. The plasma filtrate can then be removed and stored for transfusion, subjected to diagnostic tests, or further fractionated to remove pathogenic substances therein and returned to the subject as either a part, or all of the replacement fluid.

A suitable replacement fluid can be pumped from a reserve thereof (not shown) via replacement fluid pumping means 31 and replacement fluid conduit 33 and is admixed with incoming blood in inlet conduit 1. The amount of replacement fluid added to the system corresponds substantially identically in volume to the amount of fluid being removed from the system by interconnecting pumping means 31 and pumping means 29 such that they operate at substantially the same rate. This can be conveniently accomplished by providing a common drive shaft for pumping means 31 and 29, for example.

Figure 2:
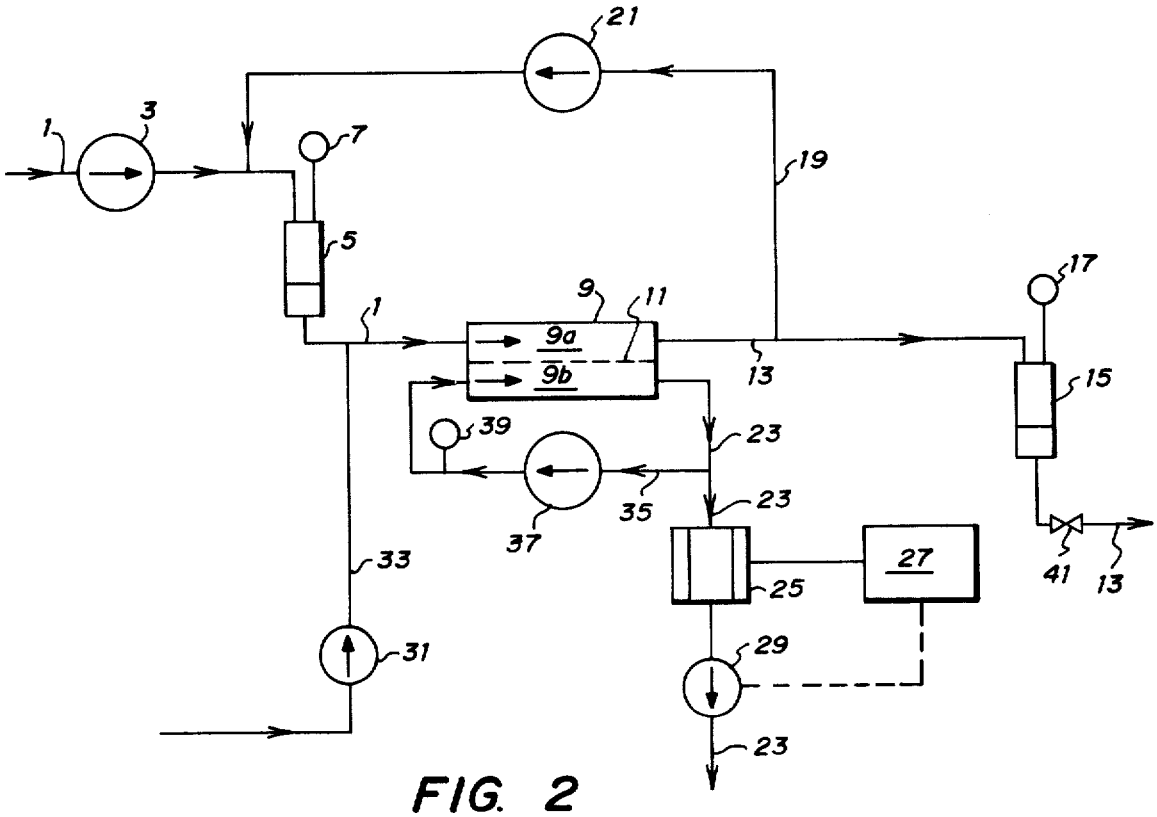

Referring to FIG. 2, a second embodiment of the present invention will be described wherein ultrafiltration rates are increased by providing a recycled flow of plasma parallel to, and in the same direction as, the flow of the blood being ultrafiltered. The schematic drawing of the process of this embodiment employs like numbers to identify like components as described hereinabove with reference to FIG. 1. Thus, whole blood from the subject enters the system via inlet conduit 1, and blood inlet pumping means 3 and the pressure thereof is indicated by pressure sensing means 7 in the manner described above with relation to FIG. 1. The blood which is to be filtered enters ultrafiltration cell 9 and flows in a path parallel to ultrafiltering membrane 11 within filtering chamber 9a. The cellular component fraction of the blood leaves ultrafiltration cell 9 via conduit 13 and a portion thereof may be recycled as needed via recycle conduit 19 and recycle pumping means 21.

The plasma fraction of the blood enters filtrate chamber 9b through ultrafilter membrane 11 and leaves filtrate chamber 9b via conduit 23 at the same end of ultrafiltration cell 9 as the cellular component fraction exits via outlet conduit 13. A portion of the plasma leaves the system (or is returned as a replacement fluid as disclosed above with reference to FIG. 1) via conduit 23 and a portion thereof is recycled via plasma recycle conduit 35 and plasma recycle pumping means 37. Thus, a portion of the plasma filtrate is recycled into the inlet end of the ultrafiltration cell such that a plasma flow parallel to, and in the same direction as, the whole blood being separated in filtering chamber 9a, occurs within filtrate chamber 9b. By adjusting the operation rate of plasma recycle pumping means 37, the pressure drop across filtrate chamber 9b (that is the difference in pressure between where plasma is introduced into filtrate chamber 9b via plasma recycle conduit 35 and where the plasma is removed via plasma outlet 23) can be controlled. Thus without affecting the blood flow rate or the shear stress at the blood-membrane interface the transmembrane pressure can be adjusted by controlling the plasma recycle flow rate. The preferred mode of operation is to adjust the pressure drop across the filtrate chamber 9b to equal the pressure drop across the filtering chamber 9a of ultrafiltration cell 9 (that is the difference between the pressure of the blood flow as it enters filtering chamber 9a from inlet conduit 1 and the pressure at the outlet of filtering chamber 9a where the fluid enters outlet conduit 13); thereby the transmembrane pressure will be approximately constant over the entire membrane. Pressure indicating means 39 and pressure sensing means 25 (such as a pressure transducer) at the inlet and outlet, respectively, of the recycle flow loop of plasma through filtering chamber 9b can be employed to monitor the pressure drop therebetween and adjust it in the above described manner.

The pressure drops across the filtering and filtrate sides of the ultrafiltration membrane can be adjusted by providing automatic adjusting mechanisms or by manually adjusting the pressure. By adjusting the clamp 41 on conduit 13 the preferred mode of operation can be obtained by adjusting the pressure indicated by pressure indicating means 17 to be approximately one half of that of pressure indicating means 7, then, by use of plasma recycle pump 37, adjusting pressure indicating means 39 to equal the pressure indicated by pressure indicating means 17 and maintaining the pressure at pressure sensing means 25 at approximately atmospheric pressure.

The ultrafiltration cell useful in the process and apparatus of the subject invention can be any one of a number of physical realizations. To achieve the arrangement and conditions of the subject invention, the membrane (or membranes) needs to be placed with respect to the filtering chamber 9a and filtrate chamber 9b so as to provide the indicated flow rates, transverse pressures, and pressure differences across the membrane. The membranes themselves can be in the form of suitably supported flat sheets, rolled-up sheets, cylinders, concentric cylinders, ducts of various cross-section, and other configurations, assembled either singly or in groups, and connected in series and/or in parallel within the ultrafiltration cell 9 so as to provide the desired flow rates and pressures. The container and the spacing material must be constructed so that there is a continuous filtering and filtrate chamber running the length of the membrane.

A preferred type of cell for use in the present invention comprises generally rectangular plate members comprising flow plates, over which the blood and filtrate flow, separated by a rectangular plate member upon which a suitable ultrafiltering membrane has been mounted. The result is a generally rectangular shaped filtering chamber allowing for a flow of blood of from about 0.01 cm to about 0.1 cm in depth to flow across the ultrafilter membrane with a filtrate chamber of approximately the same dimensions on the opposite side of the membrane. By stacking a series of these sandwiched rectangular membrane ultrafiltering cells to form a composite ultrafiltration cell, flow rates can be increased or decreased as required by the particular situation. A preferred type of rectangular ultrafiltration plate type cell is sold by Beckman Instruments Inc., Anaheim, California, under the trade name Sartorius Ultrafiltration System. This ultrafiltration cell comprises plates which have a 0.7 mm wide V-shaped parallel running grooves allowing a liquid being passed therethrough to cover the filtering area completely. This particular cell can use up to fifteen separate ultrafiltering membranes providing a maximum effected filter area of 2550 $cm^2$.

While many membranes were investigated in order to find a suitable membrane which will separate blood into cellular component and plasma fractions without substantial hemolysis or clogging problems and at a rate sufficient for the continuous operation of the system, membranes having a pore size of 0.45 microns and fabricated from cellulose nitrate or regenerated cellulose have been found to provide the necessary characteristics. Suitable membranes having these characteristics are marketed by Beckman Instruments Inc., Anaheim, California, under the trade name Sartorius Membranes.

The apparatus described in detail above can be operated in a continuous manner to separate blood into a cellular component fraction and a plasma fraction according to the following procedure. First, the instrument is filled with heparin or another suitable anticoagulant material in admixture with a saline solution. Heparin or some other suitable anticoagulant is also injected into the subject so as to prevent clogging of the system. For an adult human from about 2,000 units to about 20,000 units of heparin are employed for this purpose. Blood is then pumped from an artery or vein of the subject at a rate of from about 20 to about 400 ml/minute into the systems by blood inlet pumping means 3. As the blood goes through drip cell 5, pressure gauge 7 is used to monitor clot formation either by visual observation of the pressures indicated thereby or by means of an automatic system which will warn if pressures exceed an expected normal. After the blood has started through the membrane (or membranes if a multiple series of parallel plate membranes are being employed) recycle is started by starting recycle pumping means 21. For the Sartorius cell and membranes described above, recycle flow rates must be maintained in the range of from about 5 ml/minute/layer to about 40 ml/minute/layer in order to yield the high shear rates which are necessary to prevent damage occurring to the blood.

In a preferred embodiment, blood is returned to a vein after passing through a second drip chamber 15 which prevents air bubbles fom being entrained in the return blood. Plasma, separated from the cellular components in the blood is pumped out at exactly the same optimal rate at which it passes through the membranes by operating plasma pumping means 29 at rates such that the pressure in filtrate chamber 9b is essentially equal to atmospheric.

The following examples are submitted for the purpose of exemplifying the process and apparatus of the subject invention and are not to be construed to be limiting in any manner. Example 1 used a Dextran solution as the replacement fluid; similar experiments have been performed using plasma.

EXAMPLE 1

Employing an apparatus substantially the same as that depicted schematically in FIG. 1, a dog, weighing approximately 48 lbs., was used as an experimental subject for continuous plasmapheresis. The tubing employed was tygon, and plastic. The pumps employed were peristaltic-type pumps sold under the trade name of Sarns by Travernol and Masterflex and the ultrafiltration cell employed was the Sartorius type cell described above carrying fifteen ultrafiltering membranes having a pore size of 0.45 microns and manufactured from cellulose nitrate. The system was sterilized by formaldehyde and was flushed with a sterile saline solution prior to use. The dog was prepared for the experiment by injecting 5,500 units of heparin. The system was also flushed with heparin prior to start-up.

The dog's right femoral artery and vein were cannulated, the former providing the blood source and the later providing the return port. The blood inlet pump was then turned on, with the recycle pumping means being turned on shortly thereafter and the filtrate pumping means being turned on shortly after filtering began. The experiment was run for a total of 60 minutes during which time 1200 ml of replacement fluid (6% dextran in normal saline) was pumped into the dog and 1200 ml of plasma was separated from the dog's blood and collected. The pressures at the indicated points throughout the system at specified times during filtration are listed in Table I.

TABLE I

| Time (min) | Pressure Inlet to Membrane (mm hg) | Blood Inlet Pump (ml/min) | Recycle Pump (ml/min) | Venus Return Pressure (mm hg) | Filtrate Pump (ml/min) |
|---|---|---|---|---|---|
| 10 | 240 | 100 | 384 | 10–30 | 23.1 |
| 20 | 120 | 80 | 200 | 10–30 | 13.8 |
| 40 | 160 | 80 | 300 | 10–30 | 18.0 |
| 60 | 220 | 80 | 384 | 10–30 | 24.3 |

In Table II the initial and final concentrations of various blood constituents are given.

TABLE II

| Concentration of Various Blood Constituents | Initial | Final |
|---|---|---|
| Red Blood Cell Count | $5.9 \times 10^6$ $ml^{-1}$ | $5.1 \times 10^6$ $ml^{-1}$ |
| White Blood Cell Count | $9.9 \times 10^3$ $ml^{-1}$ | $3.5 \times 10^3$ $ml^{-1}$ |
| Platelet Count | 118,000 $ml^{-1}$ | 74,000 $ml^{-1}$ |
| IgG | 6000 mg/dl | 2920 mg/dl |
| IgM | 428 mg/dl | 202 mg/dl |
| Albumin | 2.6 gm/dl | 1.0 gm/dl |
| Cholesterol | 153 mg/dl | 58 mg/dl |
| Plasma Hemoglobin | 66 mg/dl | 75 mg/dl |

EXAMPLE 2

Employing an apparatus substantially the same as that depicted schematically in FIG. 2, expired blood from a blood bank was used in an experiment. The purpose of this experiment was to test the feasibility of using the recirculating plasma filtrate to increase the ultrafiltration rate without increasing the maximum transmembrane pressure. Two layers of cellulose nitrate membrane having a pore size of 0.45 microns were used in the Sartorius cell which had been mechanically altered to allow for parallel flow of the blood and filtrate. During this experiment the ultrafiltration rate was measured at three different transmembrane pressures for the case of recycled plasma filtrate and for the same maximum transmembrane pressures with no recycled filtrate. At all times during this experiment the plasma filtrate outlet pressure was atmospheric. The experiment's data is presented in Table III, showing the increased ultrafiltration rates obtained when recycled plasma filtrate is used.

TABLE III

| Blood Inlet Pump ml/min. | Blood Recycle Pump ml/min. | Plasma Recycle Pump ml/min. | Ultrafiltration Rate ml/min. | Blood Inlet Pressure mmHg | Blood Outlet Pressure mmHg | Plasma Inlet Pressure mmHg |
|---|---|---|---|---|---|---|
| 132 | 48 | 0 | .98 | 205 | 0 | 0 |
| 132 | 48 | 44 | 2.0 | 410 | 200 | 205 |
| 88 | 0 | 0 | .46 | 105 | 0 | 0 |
| 88 | 0 | 32 | .80 | 205 | 103 | 105 |
| 212 | 0 | 0 | .85 | 290 | 0 | 0 |
| 208 | 0 | 66 | 2.3 | 600 | 303 | 300 |

Thus, in the first set of data set forth in Table III above when the maximum transmembrane pressure was 205 mmHg and no plasma recycle was employed the ultrafiltration rate was 0.98 ml/minute. However, when the pressure drop in the filtering chamber was maintained at about 210 mmHg (Blood Inlet Pressure minus Blood Outlet Pressure) and a plasma recyle was employed to obtain a pressure drop of 205 mmHg, the ultrafiltration rate increased to 2.0 ml/minute while flow rates remained constant.

While this invention has been described in relation to its preferred embodiments, it is to be understood that various modifications thereof will be apparent to one skilled in the art upon reading the specification and it is intended to cover such modifications as fall within the scope of the appended claims.

We claim:

1. An apparatus for the continuous separation of blood into a cellular component fraction and a plasma fraction comprising:

(a) an ultrafiltration cell comprising a filter membrane having a pore size of from about 0.1 to about 1.0 microns in diameter, said membrane separating said cell into filtering and filtrate chambers, said filtering chamber comprising an inlet and an outlet, and said filtrate chamber comprising an inlet and an outlet;

(b) a blood input pumping means for pumping blood directly from a blood vessel to the inlet of said filtering chamber and delivering a flow of whole blood parallel to said filter membrane in depths of from about 0.1 mm to about 1.0 mm measured perpendicularly from the face of said membrane, and at rates sufficient to obtain a shear rate at the membrane interface of from about 10 dynes/cm$^2$ to about 1000 dynes/cm$^2$;

(c) a pumping means to direct a portion of said plasma fraction flowing from the outlet of said filtrate chamber in a flow from the inlet to the outlet of said filtrate chamber and parallel and in the same direction as the flow of whole blood passing through said filtering chamber.

2. The apparatus of claim 1 and further comprising recycle pumping means connected between the input and output of said filtering chamber for recycling a portion of the cellular component fraction from the outlet of said filtering chamber to the inlet of said filtering chamber to obtain the desired shear rate within said filtering chamber at whole blood flow rates which are not great enough to provide said shear rates.

3. The apparatus of claim 1 and further comprising a plasma pumping means connected to the outlet of said filtrate chamber.

4. The apparatus of claim 3 and further comprising pressure sensing means connected between the outlet of said filtrate chamber and said plasma pumping means for sensing the pressure in said filtrate chamber.

5. The apparatus of claim 4 and further comprising pressure regulating means interconnected to said pressure sensing means and said plasma pumping means for regulating the operation rate of said plasma pumping means in response to variations of filtrate chamber pressures as sensed by said pressure sensing means.

6. The apparatus of claim 3 and further comprising replacement fluid pumping means connected to the inlet of said filtering chamber for delivering a volume of replacement fluid to said filtering chamber at volumetric rates substantially equal to the volume of plasma fraction leaving said filtrate chamber.

7. The apparatus of claim 6 wherein said replacement fluid pumping means and said plasma pumping means are interconnected so as to operate at substantially the same rate and thereby provide for the addition of a replacement fluid to said filtering chamber at the same rate as the plasma fraction is being removed from said filtrate chamber by said plasma pump.

8. The apparatus of claim 1 and further comprising drip cell means for removing entrapped gases from the blood being separated, a first said drip cell means communicating with the inlet of said filtering chamber and a second drill cell means communicating with the outlet of said filtering chamber.

9. The apparatus of claim 8 and further comprising pressure indicating means, a first said pressure indicating means communicating with the inlet of said filtering chamber and a second said pressure indicating means communicating with the outlet thereof.

10. The apparatus of claim 1 and further comprising pressure indicating means communicating with the inlet of said filtrate chamber.

11. The apparatus of claim 1 and further comprising flow restriction means communicating with the outlet of said filtering chamber for regulating the rate of flow from said outlet and thereby the pressure within said filtering chamber.

12. The apparatus of claim 1 wherein said filter membrane has a pore size of about 0.45 microns and is fabricated from materials selected from the group consisting of cellulose nitrate and regenerated cellulose.

13. An apparatus for the continuous separation of blood into a cellular component fraction and a plasma fraction comprising:

(a) an ultrafiltration cell comprising a filter membrane having a pore size of from about 0.1 to about 1.0 microns in diameter separating said cell into filtering and filtrate chambers, said filtering chamber having an inlet and an outlet and said filtrate chamber having an outlet;

(b) blood input pumping means for pumping blood directly from a blood vessel to the inlet of said filtering chamber and delivering a flow of whole blood parallel to said filter membrane in depths of from about 0.1 mm to about 1.0 mm, measured perpendicularly from the face of said membrane;

(c) recycle pumping means connected between the inlet and outlet of said filtering chamber for recycling a portion of said blood fraction from said outlet to said inlet the combined flow rates of said o the outlet of said filtrate chamber for removing said plasma fraction from said filtrate chamber;

(e) replacement fluid pumping means connected to the inlet of said filtering chamber for delivering replacement fluid thereto at substantially the same volumetric rate at which said plasma fraction is being removed from said filtrate chamber via said plasma pumping means.

14. The apparatus of claim 13 and further comprising pressure sensing means connected between the outlet of said filtrate chamber and said plasma pumping means for sensing pressure in said filtrate chamber, and automatic pressure regulating means interconnected between said pressure sensing means and said plasma pumping means for regulating the pumping rate of said pumping means in response to variations in pressure sensed by said pressure sensing means.

15. The apparatus of claim 13 wherein said replacement fluid pumping means and said plasma pumping means are interconnected so as to operate at substantially the same rate to thereby provide for delivery of replacement fluid to said filtering chamber at the same volumetric rate at which said plasma fraction is removed from said filtrate chamber.

16. The apparatus of claim 13 and further comprising drip cell means for removing entrapped gas in blood being separated, a first drip cell means communicating with the inlet of said filtrate chamber and a second drip cell means communicating with the outlet thereof.

17. The apparatus of claim 16 and further comprising pressure indicating means, a first said pressure indicating means communicating with the inlet of said filtering chamber and a second said pressure indicating means communicating with the outlet of said filtering chamber.

18. The apparatus of claim 13 wherein said filter membrane has a pore size of about 0.45 microns and is fabricated from materials selected from the group consisting of cellulose nitrate and regenerated cellulose.

19. A continuous plasmapheresis process comprising:

(a) continuously withdrawing whole blood from the blood vessel of a donor and pumping said whole blood into the filtering chamber of an ultrafiltration cell;

(b) continuously filtering said whole blood into a cellular component fraction and a plasma fraction by passing it in a flow over and parallel to an ultrafilter membrane having a pore size of from about 0.1 to 1.0 microns in diameter, and at a flow rate sufficient to provide a shear stress at the membrane interface of from about 10 dynes/cm$^2$ to about 1000 dynes/cm$^2$ at transmembrane pressures of from about 50 mm of mercury to about 700 mm of mercury;

(c) continuously admixing said cellular component fraction with an amount of replacement fluid substantially equal to said separated plasma fraction; and (d) continuously returning said cellular component fraction and replacement fluid mixture to a blood vessel of said donor.

20. The process of claim 19 and further comprising recycling a portion of the plasma fraction separated from said whole blood in a flow parallel to and in the same direction as the flow of said whole blood over said ultrafilter membrane, but on the opposite side of said membrane from the flow of whole blood, to thereby obtain a substantially uniform transmembrane pressure across the entire length of said membrane.

21. The process of claim 19 and further comprising recycling a portion of said cellular component fraction over said ultrafilter membrane in the same direction as said flow of whole blood in a manner such that said shear rates can be obtained at insufficient whole blood flow rates.

22. The process of claim 19 wherein said transmembrane pressure is from about 100 to about 400 mm of mercury.

23. The process of claim 19 wherein said ultrafiltration is effected employing an ultrafilter membrane having a pore size of about 0.45 microns and fabricated from materials selected from the group consisting of cellulose nitrate and regenerated cellulose.

24. The process of claim 19 wherein said shear stress at the membrane interface is from about 150 dynes/cm$^2$ to about 600 dynes/cm$^2$.

*25. Apparatus for plasmapheresis treatment of a patient, comprising:*

*(a) an ultrafiltration cell having an inlet for receiving a flow of whole blood, an outlet for discharging blood cellular components, and an outlet for discharging plasma filtrate;*

*(b) means disposed in said ultrafiltration cell for effecting separation of plasma and cellular components of whole blood flowing therein;*

*(c) means for continuously withdrawing whole blood from a blood vessel of a patient and supplying same to the whole blood inlet of said cell;*

*(d) means coupled to the blood cellular components outlet, for continuously receiving the separated blood cellular components and supplying same back to the patient; and*

*(e) means coupled to the plasma filtrate outlet, for continuously removing plasma filtrate therefrom.*

*26. The apparatus of claim 25 further comprising:*

*means in fluid communication with the whole blood inlet to said cell, for supplying a continuous flow of replacement fluid to be admixed with whole blood incoming to the whole blood inlet.*

*27. Apparatus for plasmapheresis treatment of a patient, comprising:*

*(a) an ultrafiltration cell having a filter membrane defining filtering and filtrate chambers, said filtering chamber having an inlet and an outlet, and said filtrate chamber having an outlet unconnected with the filtering chamber outlet;*

*(b) means for continuously withdrawing whole blood from a blood vessel of a patient and supplying same to the filtering chamber inlet, and establishing a parallel flow across said filter membrane at a rate sufficient to produce a shear rate at the membrane interface that effects separation of plasma and blood cellular components without hemolysis;*

*(c) means coupled to the filtering chamber outlet, for continuously receiving the separated blood cellular components and supplying same back to the patient; and*

*(d) means coupled to the filtrate chamber outlet, for continuously removing the separated plasma fraction from the filtrate chamber.*

*28. The apparatus of claim 27 further comprising:*

*means in fluid communication with the filtering chamber inlet, for supplying a continuous flow of replacement fluid to be admixed with whole blood incoming to the filtering chamber.*

* * * * *